United States Patent [19]

Kato et al.

[11] Patent Number: 4,895,959

[45] Date of Patent: Jan. 23, 1990

[54] PURIFICATION OF N-METHYL-2-PYRROLIDONE

[75] Inventors: Toshikazu Kato; Hiroshi Inoue; Kensuke Ogawara, all of Mie, Japan

[73] Assignees: Tosoh Corporation, Amaguchi; Toso Steel Co., Ltd., Tokyo, both of Japan

[21] Appl. No.: 363,692

[22] Filed: Jun. 9, 1989

[30] Foreign Application Priority Data

Jun. 10, 1988 [JP] Japan ............................ 63-141613

[51] Int. Cl.$^4$ ........................................ C07D 207/267
[52] U.S. Cl. .................................................... 548/555
[58] Field of Search ......................................... 548/555

[56] References Cited

U.S. PATENT DOCUMENTS

| | | | |
|---|---|---|---|
| 2,939,869 | 6/1960 | Carlson | 548/555 |
| 3,354,129 | 11/1967 | Edmonds et al. | 260/79 |
| 3,687,907 | 8/1972 | Crouch et al. | 548/555 |
| 4,472,585 | 9/1984 | Cleary | 548/555 |
| 4,501,902 | 2/1985 | Cleary | 548/555 |
| 4,510,316 | 4/1985 | Cleary et al. | 548/555 |
| 4,831,160 | 5/1989 | Leighton | 548/555 |

FOREIGN PATENT DOCUMENTS 62-145061  6/1987  Japan .

*Primary Examiner*—David B. Springer
*Attorney, Agent, or Firm*—Sughrue, Mion, Zinn, Macpeak & Seas

[57] ABSTRACT

A method for purifying N-methyl-2-pyrrolidone containing thiophenol and/or diphenyl disulfide is disclosed, comprising adding a polyhalogenated aromatic compound and an alkali metal hydroxide and/or an alkali metal carbonate to the N-methyl-2-pyrrolidone containing thiophenol and/or diphenyl disulfide, heat treating the mixture, and subjecting the mixture to separation by distillation. The thiophenol and/or diphenyl disulfide can be removed with ease and at low cost.

5 Claims, No Drawings

PURIFICATION OF N-METHYL-2-PYRROLIDONE

FIELD OF THE INVENTION

This invention relates to purification of N-methyl-2-pyrrolidone and, more particularly to a method for removing thiophenol and/or diphenyl disulfide from N-methyl-2-pyrrolidone containing them.

BACKGROUND OF THE INVENTION

N-Methyl-2-pyrrolidone is an organic polar solvent excellent in heat stability and chemical stability and is therefore widely utilized as a chemical reaction medium, recrystallization medium, or a cleaning agent.

In particular, N-methyl-2-pyrrolidone is useful as a reaction solvent in the reaction between dihalogenated aromatic compounds and alkali metal sulfides for the synthesis of polyarylene sulfides as disclosed in JP-B 45-3368 (the term "JP-B" as used herein means an "examined published Japanese patent application"). It has been industrially employed as a polymerization solvent for obtaining polyphenylene sulfide (hereinafter abbreviated as PPS), one of the polyarylene sulfides.

The above-described process for producing PPS is frequently attended by by-production of thiophenol or diphenyl disulfide, and use of N-methyl-2-pyrrolidone containing the by-products thiophenol and/or diphenyl disulfide as a polymerization solvent results in serious reduction of molecular weight of the resulting polymers.

In addition, thiophenol or diphenyl disulfide is liable to form a complex compound with N-methyl-2pyrrolidone so that distillation of the spent solvent is not sufficient for separation of the thiophenol or diphenyl disulfide from N-methyl-2-pyrrolidone.

However, no study has been made as yet on purification of N-methyl-2-pyrrolidone containing thiophenol or diphenyl disulfide.

SUMMARY OF THE INVENTION

As a result of extensive investigations, the inventors have found that N-methyl-2-pyrrolidone containing thiophenol and/or diphenyl disulfide can easily be purified by adding a polyhalogenated aromatic compound and an alkali metal salt to the N-methyl-2pyrrolidone, heat-treating the mixture, and subjecting the mixture to separation by distillation. The present invention has been completed based on this finding.

This invention provides a method of purifying N-methyl-2-pyrrolidone containing thiophenol and/or diphenyl disulfide which comprises adding a polyhalogenated aromatic compound and an alkali metal hydroxide and/or an alkali metal carbonate to the N-methyl-2 pyrrolidone, heat-treating the mixture, and subjecting the mixture to separation by distillation.

DETAILED DESCRIPTION OF THE INVENTION

The polyhalogenated aromatic compound which can be used in the present invention is an aromatic compound containing at least two halogen atoms per molecule. Specific examples of the polyhalogenated aromatic compound include p-dichlorobenzene, m-dichlorobenzene, o-dichlorobenzene, p-dibromobenzene, p-diiodobenzene, dichloronaphthalene, dibromonaphthalene, dichlorodiphenylsulfone, dichlorobenzophenone, dichlorodiphenyl ether, dichlorodiphenyl sulfide, dichlorodiphenyl, dibromodiphenyl, dichlorodiphenyl sulfoxide, dichlorobenzonitrile, dichlorobenzoic acid, trichlorobezene, tribromobenzene, tetrachlorobenzene, trichloronaphthalene, tetrachloronaphthalene, and mixtures thereof.

The amount of the polyhalogenated aromatic compound to be added ranges from 0.3 to 5, preferably from 0.5 to 3, in molar ratio to the total amount of thiophenol and diphenyl disulfide present in the N-methyl-2-pyrrolidone. If the molar ratio is less than 0.3, the effect to remove thiophenol and/or diphenyl disulfide would be insufficient. Molar ratios exceeding 5 are uneconomical.

The alkali metal hydroxide which can be used in the present invention includes lithium hydroxide, sodium hydroxide, and potassium hydroxide.

The alkali metal carbonate which can be used in the present invention includes lithium carbonate, sodium carbonate, and potassium carbonate.

The amount of the alkali metal hydroxide and/or alkali metal carbonate to be used usually ranges from 0.5 to 5, preferably from 0.9 to 3, in molar ratio to the total amount of thiophenol and diphenyl disulfide present in the N-methyl-2-pyrrolidone. If it is less than 0.5, the effect to remove thiophenol and/or diphenyl disulfide would be insufficient. Molar ratios exceeding 5 are uneconomical. The alkali metal salt can be added in the form of a solid or an aqueous solution.

Conditions for the heat treatment according to the present invention are subject to variation depending on the kind of the polyhalogenated aromatic compound added. In general, the heat treatment is performed at a temperature ranging from 100 to 300° C., preferably from 150 to 270° C., for a period of from 0.1 to 10 hours. Heating temperatures lower than 100° C. result in an increase of treating time, and those higher than 300° C. cause decomposition of N-methyl-2-pyrrolidone.

The separation by distillation can be effected by means of known distillation apparatus, such as atmospheric pressure distillation apparatus and vacuum distillation apparatus.

The present invention is now illustrated in greater detail by way of the following Examples and Comparative Examples, but it should be understood that the present invention is not deemed to be limited thereto.

In these examples, the contents of thiophenol and diphenyl disulfide in the N-methyl-2-pyrrolidone both to be purified and recovered were determined by gas chromatography. All the percents are given by weight unless otherwise indicated.

EXAMPLE 1

In a 500 ml-volume autoclave equipped with a stirrer were charged 300 g of N-methyl-2-pyrrolidone (hereinafter abbreviated as NMP) containing 5700 ppm (15.5 mmols) of thiophenol (hereinafter abbreviated as TP) and 1900 ppm (2.6 mmols) of diphenyl disulfide (hereinafter referred to as DPDS), 5.32 g (36.2 mmols) of p-dichlorobenzene, and 6.4 g (36.2 mmols) of sodium hydroxide (20% aqueous solution), and the mixture was heat-treated at 250° C. for 3 hours while stirring. After cooling, the mixture was subjected to distillation under atmospheric pressure in a glass-made distillation apparatus to thereby recover 282 g of NMP.

The recovered NMP was found to contain 370 ppm of TP and no DPDS by gas chromatography.

COMPARATIVE EXAMPLE 1

The same procedure of Example 1 was repeated, except for adding neither p-dichlorobenzene nor sodium hydroxide and conducting no heat treatment. As a result, 289 g of NMP was recovered but was found to contain 5400 ppm of TP and 1400 ppm of DPDS, proving virtually unpurified.

EXAMPLE 2

The same procedure of Example 1 was repeated, except that a mixture of 300 g of NMP containing 5.5% (150 mmols) of TP and 1.5% (21 mmols) of DPDS, 25.1 g (171 mmols) of p-dichlorobenzene, and 13.7 g (171 mmols) of sodium hydroxide (50% aqueous solution) was heat treated at 230° C. for 2 hours. As a result, 273 g of NMP was recovered, which was found to have a TP concentration of 1.6% and a DPDS concentration of 60 ppm.

EXAMPLE 3

The same procedure of Example 1 was repeated, except for using 6.57 g (36.2 mmols) of trichlorobenzene in place of p-dichlorobenzene. As a result, 291 g of NMP was recovered, which was found to have a TP concentration of 150 ppm and contain no DPDS.

EXAMPLE 4

The same procedure of Example 1 was repeated, except for using 38.4 g (36.2 mmols) of sodium carbonate (10% aqueous solution) in place of sodium hydroxide. As a result, 292 g of NMP was recovered, which was found to have a TP concentration of 510 ppm and a DPDS concentration of 50 ppm.

COMPARATIVE EXAMPLE 2

The same procedure of Example 1 was repeated, except that sodium hydroxide was not added. As a result, 285 g of NMP was recovered, which was found to have a TP concentration of 3500 ppm and a DPDS concentration of 1100 ppm.

COMPARATIVE EXAMPLE 3

The same procedure of Example 1 was repeated, except that p-dichlorobenzene was not added. As a result, 284 g of NMP was recovered, which was found to have a TP concentration of 5100 ppm and a DPDS concentration of 1300 ppm.

As described above, the present invention makes it possible to remove thiophenol and/or diphenyl disulfide contained in N-methyl-2-pyrrolidone with ease and at low cost, thus having high industrial value.

While the invention has been described in detail and with reference to specific embodiments thereof, it will be apparent to one skilled in the art that various changes and modifications can be made therein without departing from the spirit and scope thereof.

What is claimed is:

1. A method of purifying N-methyl-2-pyrrolidone containing thiophenol and/or diphenyl disulfide which comprises adding a polyhalogenated aromatic compound and an alkali metal hydroxide and/or an alkali metal carbonate to the N-methyl-2-pyrrolidone containing thiophenol and/or diphenyl disulfide, heat-treating the mixture, and subjecting the mixture to separation by distillation.

2. A method as claimed in claim 1, wherein said polyhalogenated aromatic compound is p-dichlorobenzene or trichlorobenzene.

3. A method as claimed in claim 1, wherein said polyhalogenated aromatic compound is added in a molar ratio of from 0.3 to 5 with respect to the total amount of thiophenol and diphenyl disulfide in the N-methyl-2pyrrolidone.

4. A method as claimed in claim 1, wherein said alkali metal hydroxide and/or alkali metal carbonate is or are added in a total molar ratio of from 0.5 to 5 with respect to the total amount of thiophenol and diphenyl disulfide in the N-methyl-2-pyrrolidone.

5. A method as claimed in claim 1, wherein said heat treating is at a temperature of from 100 to 300° C. for a period of from 0.1 to 10 hours.

* * * * *